United States Patent
Ansorge et al.

(10) Patent No.: US 6,428,668 B1
(45) Date of Patent: Aug. 6, 2002

(54) SAMPLER TRANSFER

(75) Inventors: Wilhelm Ansorge, Gaiberg; Holger Erfle, Sandhausen, both of (DE)

(73) Assignee: Europaisches Laboratorium fur Molekularbiologie (EMBL), Heidelberg (DE)

( * ) Notice: Subject to any disclaimer, the term of this patent is extended or adjusted under 35 U.S.C. 154(b) by 0 days.

(21) Appl. No.: 09/350,090

(22) Filed: Jul. 9, 1999

Related U.S. Application Data (63) Continuation-in-part of application No. PCT/EP98/00130, filed on Jan. 12, 1998.

(30) Foreign Application Priority Data

Jan. 10, 1997 (DE) ................................. 197 00 626.4

(51) Int. Cl.$^7$ ................................................. G02N 27/26
(52) U.S. Cl. ........................ 204/466; 204/456; 204/467; 204/606; 204/616; 435/287.7; 435/309.1; 422/100
(58) Field of Search ............................. 204/450, 456, 204/466, 467, 600, 606, 616, 617, 618; 435/287.7, 309.1; 422/100; 73/864.72; 600/575

(56) References Cited

U.S. PATENT DOCUMENTS

| | | | |
|---|---|---|---|
| 5,064,519 A | 11/1991 | Tice, Jr. et al. | 204/182 |
| 5,284,565 A | 2/1994 | Chu et al. | 204/229 |
| 5,405,516 A | 4/1995 | Bellon | 204/180 |
| 5,464,515 A | 11/1995 | Bellon | 204/182 |
| 6,048,982 A | * 4/2000 | Waggoner | 548/148 |

FOREIGN PATENT DOCUMENTS

| | | |
|---|---|---|
| DE | 30 16 682 | 11/1980 |
| DE | 30 24 288 | 3/1982 |
| DE | 38 05 808 | 9/1989 |
| EP | 0 464 544 | 6/1991 |
| EP | 0 475 164 | 8/1991 |
| WO | 92/10518 | 6/1992 |
| WO | 94/11529 | 5/1994 |
| WO | 95/10559 | 1/1995 |
| WO | 96/27787 | 9/1996 |

OTHER PUBLICATIONS

Webster et al., "Monolithic Capillary Gel Electrophoresis Stage With On–Chip Detector", IEEE, pp. 491–496.

* cited by examiner

*Primary Examiner*—Jill Warden
*Assistant Examiner*—Alex Noguerola
(74) *Attorney, Agent, or Firm*—Arent Fox Kintner Plotkin Kahn PLLC (57) ABSTRACT

In the method moving a sample substance by means of a sample feeder (26) form a sample pickup site to a delivery site (20) of a sample processor (10), the invention proposes fitting the sample feeder (26) with at least one porous material element having a pore size such that the sample substance shall be kept in the liquid phase in the porous material at least during sample pickup by the sample feeder (26) and during sample delivery to the sample processor (10).

41 Claims, 4 Drawing Sheets

SAMPLER TRANSFER

CROSS REFERENCE TO RELATED APPLICATION

This application is a continuation-in-part of International Application PCT/EP98/00130, filed Jan. 12, 1998, and designating the U.S.

DESCRIPTION

The invention relates to a method for moving a sample substance by a sample feeder from a sample pickup site to a sample delivery site of a sample processor, preferably a sample analyzer.

In a known procedure (German patent document A1 38 05 808, FIGS. 10, 11), the sample substance is withdrawn by a pipetting system from a sample-vial rack and moved to the sample processor in the form of a vertically oriented electrophoresis apparatus. Moreover several samples may be picked up simultaneously using a corresponding number of pipets and be fed into corresponding sample wells at the upper gel edge. This known sample feeder system is mechanically highly complex, the more so when very thin gel layers are being used and at the same time a large number of samples must be analyzed. The gap between the glass plates subtended by the gel thickness presently is less than a mm for the desired gel thicknesses; the separation between consecutive sample sockets is a few mm. Depending on gel width, up to 100 sample wells may be arrayed adjacently. The complexity is correspondingly high for such a number of pipets, and so are the requirements of positional accuracy. In practice the gel can only be oriented vertically because otherwise the sample wells might leak.

A procedure of the initially cited kind is known from the patent document WO 94/11529. The sample substance is chemically specifically bonded to the teeth of the comb-shaped sample feeder. After the sample feeder has been moved to the electrophoresis gel, the specific chemical bond is dissolved by adding an appropriate means (formamide), whereby the sample substance then is able to detach from the sample feeder and able to penetrate the gel under the action of the electric field. The comb-shaped feeder only comprises 8 teeth and accordingly only eight samples can be analyzed simultaneously. This feature may be due to the fact that only comparatively wide teeth allow providing sufficient sample substance.

The objective of the invention is to create a method of the cited kind to allow effective and simple sample transport.

This problem is solved in that the sample feeder comprises at least one porous material element of such pore size that the sample substance is kept in the liquid state by capillary forces in the said porous material at least when the sample is picked up by the sample feeder and when the sample is delivered to the sample processor. Accordingly the sample substance is kept in the liquid state merely by capillary forces during sample pickup or sample delivery. In the interim, the sample substance is present, though not mandatorily, in dried form in the pores of the porous material. In any event complex mechanisms such as multi-pipeting systems are eliminated. As regards sample delivery, the porous material need only be brought into contact with the sample substance in the liquid state; no reactions to chemically bond the sample substance to the sample feeder are at all required, nor are the chemical reactions during sample delivery to dissolve the chemical bond between sample substance and sample feeder. Because the capillary forces keep the sample substance in the liquid state during sample transport until transfer into the sample processor, and this regardless of the direction of gravity, restrictions no longer are incurred on the orientation of the sample processor. The porous material may be laminar and thus may be inserted in problem-free manner between the glass plates of a gel electrophoresis apparatus. At least the material part of the sample feeder consists preferably entirely of a porous material, as a result of which the capacity of the material element for the sample substance shall be relatively high. Therefore it is enough to use small-format material elements to allow a corresponding plurality of compactly configured material elements. For a given width of the electrophoretic gel, the number of the samples which must be analyzed simultaneously can therefore be significantly raised, for instance to 192, even 384 samples.

In a further development of the invention, following sample pickup by the feeder, the sample is dried and the feeder is moved into a liquid phase before the sample is delivered. The sample feeder dried in the interim is especially easily manipulated; the danger of interim contamination is substantially reduced.

To constrain the sample feeder to deliver the sample to the sample processor, the sample feeder can be processed, for instance mechanically, illustratively being mechanically compressed, or compressed air being blown through it. However, in especially preferred manner, an electrical field is generated in the zone of the sample delivery site to cross the material element in order to generate a current of electrically charged molecules, macromolecules or particles of the sample substance from the porous material element into the sample processor. The electric field intensity is selected in such manner as a function of electric charge that the capillary forces are overcome. The use of this method stage is especially advantageous in electrophoresis because it including anyway means for electric field generation.

The sample feeder loaded with the sample substance being especially easily manipulated as indicated above, there follows the advantageous option to move the sample feeder, once loaded with sample, from the sample pickup site to the sample delivery site. Thus the sample can be picked up at a site arbitrarily away from the sample processor apparatus.

Alternatively however the sample also may be moved from the sample pickup site to the sample delivery site in that, provided there be physical connection implemented by the porous material element of the sample pickup site between the sample pickup and delivery sites, the capillary forces shall ensure sample transport. This kind of sample feeding process is used foremost when the sample delivery site is unduly inaccessible or highly compact, for instance as regards microchip sensors, in particular DNA sensors. In such cases a separate material element, independent of the others' material elements, is used for each sample, so as to avoid cross-talk, that is mixing of sample substance, from the beginning, an event which otherwise, in the light of the comparatively large quantities of sample substance involved, might occur.

However the feasibility of mixing also may be exploited in controlled manner in that the porous material will be wetted at different sites or consecutively at the same site with the substances to be mixed. Illustratively, by appropriate additions, proteins (for instance antigens) may be mixed in the porous material with antibodies, or DNA with complementary hybridization DNA or DNA with labeling means.

Comparatively small amounts of sample substance may be used in the first above alternative of physical transport of the sample feeder from the sample pickup site to the sample delivery site, and consequently the danger of crosstalk in general can be disregarded also where connected material elements are involved.

Because of the above easy handling and the comparatively high capacity for sample substance of the porous material element, a preferred feasibility is offered, namely a sample processor comprising a plurality of sample delivery sites operates with a corresponding plurality of porous material elements.

As already mentioned, separate material elements may be used each time, the method comprising rigorous separation without danger of crosstalk. However the manufacture and handling of the material elements will be substantially simplified if the sample feeder of the invention comprises one material element support bearing the material elements in an array corresponding to the configuration of the sample pickup sites. The sample feeder in this design may be substantially like a comb when the sample pickup sites are confined in linear or arcuate manner.

The sample feeder can be manufactured in especially simple manner, for instance by stamping, if it includes a sheet of porous material comprising all porous material elements.

However the material element support also may bear a corresponding plurality of mutually separate material elements. Such a geometry is preferred when danger of crosstalk cannot be excluded otherwise.

The material element support may be in the form of a substrate sheet or also be of another design, for instance like a clamp.

A porous material with a mean pore size less than $100\mu$, preferably less than $10\mu$, most preferred less than $1\mu$, is used, resp. with a mean pore size between 1.5 and $0.2\mu$, best of all of about $0.5\mu$. Such a porous material offers adequate capillary force for the conventional sample substances used in particular in biochemistry.

It has been found that in particular a porous material made of porous cellulose acetate or porous polyethylene or porous glass or agarose gel or other wide-mesh gel matrices is well suited.

Sample delivery to the sample processor in the presence of said electric field requires that the moved substances be electrically charged. This charge may be generated in biological macromolecules in the required manner by adjusting the pH value of the liquid phase in appropriate manner.

It was discovered that under the effect of the electric field, almost all the sample substance is delivered from the sample feeder to the sample processor. As a result the sample feeder may be used repeatedly in sequence to deliver sample liquid. Again the complexity of implementing the method of the invention is reduced by this feature.

To facilitate loading the sample feeder with a plurality of samples, the invention proposes using a sample-vessel rack comprising a number of sample wells in a geometry corresponding to the configuration of the material elements of the feeder. As a result it is enough that the illustratively comb-shaped sample feeder dips simultaneously with all its comb-teeth into the plurality of sample wells.

The above described method is applicable in a number of sample processors, in particular to detect and/or to manufacture biochemical reaction products. Another application is a mass spectrometer. A preferred application is delivering sample liquids to an electrophoretic or chromatographic apparatus.

The separator, preferably the separation gel of the electrophoretic apparatus, furthermore may be oriented, not only vertically in the heretofore conventional manner, but also horizontally or in any direction.

The invention furthermore proposes that a liquid phase, preferably a buffer solution, be added at one zone at a loading end of a separator of the electrophoretic or chromatographic apparatus, namely before or after the sample feeder has been moved near. In the case of a sample feeder that in the meantime was dried, the liquid phase dissolves the sample substance that was reversibly adsorbed in the pores inside these pores. The resulting capillary forces then retain the sample substance in the pores as long as no external forces, such as the electric field forces of the electrophoretic apparatus, arise. By adding the liquid phase, in particular the buffer solution, the earliest onset of migration of the sample substance can be determined; this will also be the case if the sample substance was not dried in the meantime.

The electric field effect allows immediate transfer of the sample substance into the separator; however, because of the presence of the liquid phase, preferably a buffer solution, a gap up to several mm also can exist between the sample feeder and the loading end of the separator.

The invention further proposes that with respect to a separator appropriate to simultaneously separate several sample liquids and with several sample-liquid pickup sites along an edge of the separator, the sample-liquid pickup sites form sample-liquid wells in the separator to receive corresponding porous material elements of the sample feeder. The sample-liquid wells may be made in this respect independently of the sample feeder and before the sample feeder is brought near, or, alternatively, by seating the comb-shaped sample feeder already fitted with sample substance in the separation gel before latter is polymerized.

The sample-liquid clearances inherently prevent mixing different samples at the edge of the separator.

It was found however that using a separator appropriate for a simultaneous separation procedure and with several sample pickup sites along the edge of the separator, the sample feeder can be made to contact the edge of the separator or be mounted at a gap of several mm from this edge. In this case there are no sample-liquid wells and the separator terminates continuously along the straight or arcuate edge of the separator. This design facilitates the preparation of the separator. It was further discovered that the linear sample density (parallel to the edge of the separator) can be further increased on account of the elimination of the strips of gel between the wells, without thereby degrading measurement, in particular without danger of sample-mixing. Moreover precise, mutually parallel electrophoretic tracks are generated allowing accurate comparative analysis of adjacent tracks, the more so in the invention the beginning of electrophoresis of each track can be triggered with accurate simultaneity. The cause of such significant advantages may be that in the invention, the discharge of sample substance from the sample feeder and hence the entry into the electrophoretic gel is triggered solely by the electric field with constrained migration of the charged particles in the direction of the field. A motion of a different kind, in particular transverse diffusion, is suppressed from the start.

The above described advantages of the invention also apply at least in part when relating to delivering sample liquid to an electrophoretic or chromatographic apparatus comprising one or more separation capillaries. In this case, too, high sample density and simple handling can be achieved.

As already indicated, the method of the invention can be used to deliver sample liquid to a microchip system, in which case the sample feeder(s) also may be stationary separate material elements in order to permanently connect inaccessible sensor zones, for instance 2 mm×2 mm in size, to more accessible delivery sites.

Moreover the invention concerns a sample feeder with which to carry out the above cited method comprising at least one material element of appropriately porous nature.

Furthermore the invention relates to an electrophoretic apparatus comprising a sample feeder to carry out the said method, where, as already discussed, a horizontal configuration, or an arbitrary configuration of the separation gel is possible in addition to the heretofore conventional one.

Another aspect of the invention concerns a method whereby to carry out a reaction between at least a first co-reactant and at least a second co-reactant, preferably to detect and/or to prepare a biochemical reaction product in a sample liquid, said method being characterized in that at least one first co-reactant reversibly adsorbed on a porous material is made to contact at least one second co-reactant in a liquid phase, the pore size of the porous material being such that the liquid phase is retained at least in part in the porous material by capillary forces.

Preferably the reaction in the just-above described method is biochemical, that is it is a reaction in which participate biological macromolecules for instance proteins, glycoproteins and/or nucleic acids or complexes of such macromolecules, for instance immunity complexes between antibodies and antigens, protein/nucleic-acid complexes or nucleic-acid/hybridization complexes as co-reactants or in which such are reaction products. This method is especially well suited for reaction at nucleic acids, for instance an in-vitro transcription, a nucleic-acid sequencing or a nucleic-acid amplification.

In the method described just above, a first co-reactant is used which is reversibly adsorbed on a porous material of appropriate pore size, that is, adsorption on a porous material does not take place by chemical, covalent bonds or by high-affinity interactions (for instance biotin-streptavidin), and accordingly elution of the first co-reactant and/or of the reaction products from the porous material essentially succeeds completely under appropriate conditions.

Moreover several first co-reactants may be adsorbed to the porous material: for instance the material may be impregnated with a liquid containing several co-reactants or the material may be impregnated consecutively or at different sites with several liquids.

In the method of the invention, the porous material may be used in such manner that the first co-reactant is adsorbed to it in dry or moist form. To improve the stability of the adsorbed co-reactant or to improve the volume of reaction, dry adsorption is preferred. Drying of the porous material may be carried out conventionally, for instance by freeze- or vacuum-drying.

In one implementation of the method of the invention, the reaction is a testing reaction to detect an analyte in a biological sample, for instance a sample including a body fluid such as serum, blood, plasma, urine, saliva etc. Other biological samples such as tissue samples also may be used.

In the testing reaction detecting an analyte, the first co-reactant reversibly adsorbed on the porous material preferably is a substance able to specifically bond to the analyte to be determined or it may be a substance competing with the analyte for a further bonding partner. If for instance the analyte is an immunochemically detectable antigen, the first co-reactant may be an antibody bondable to the analyte or an analyte-analogue able to compete with the analyte to bond to an antibody. If illustratively the analyte is a nucleic acid, the first co-reactant may be a nucleic acid complementary to the analyte or a corresponding nucleic-acid/analogue (for instance a peptide nucleic acid).

In detection procedures, a labeling group appropriately is present during the reaction to indicate the occurrence and/or the intensity of the reaction and thereby to allow qualitative or quantitative determination of the analyte. Preferably the labeling group shall be non-radioactive, for instance being a fluorescent or luminescent group, an enzyme, a metal particle, an NMR-active group or another in the field of biochemical detection procedures familiar to the expert.

In a preferred implementation of the invention, the reaction is carried out in such manner that the reaction products are essentially wholly held inside the pores. Also in preferred manner, the reaction products are essentially wholly removable from the porous material. In this manner it is possible to carry out quantitative reaction analysis.

As described above, the sample liquid containing the reaction product may be delivered to a sample processor, preferably a sample analyzer.

Another advantage of carrying out a reaction of the invention in the pores of a porous material is that after the desired time of reaction it is not necessary to add a non-aqueous stop or denaturing reagent such as formamide. As regards the procedures of the state of the art, in particular reactions at nucleic acids, such a formamide reagent must be added to achieve adequate denaturation of the nucleic acids present in the sample. Surprisingly it was discovered that this addition of formamide is unnecessary in the method of the invention.

Another object of the invention is a reagent to carry out a reaction in particular to detect and/or to prepare a biochemical reaction product and comprising at least one part with a material element of porous material, at least one reactive substance being reversibly adsorbed on the porous material and the pore size of this porous material being such that upon contact with liquid, the reactive substance shall be held at least partly in the porous material by capillary forces. This reagent of the invention can be used besides other test components as an ingredient of a reagent kit.

The invention also relates to an electrophoretic apparatus fitted with a porous and preferably comb-shaped sample feeder, comprising a separator, preferably a separation gel, and an electric-field system to apply an electric field to the separator.

Such apparatus is known per se (U.S. Pat. No. 5,464,515 and European patent document A10,493,996). All teeth of the comb-shaped porous sample feeder make bodily contact with the gel at at least one point to assure the transfer of the sample substance (here proteins) into the gel. However heretofore such apparatus did not prove wholly satisfactory.

The objective of the invention is to create an electrophoretic apparatus of the said kind which shall offer improved measurements, in particular resolution.

This problem is solved in that the porous sample feeder used in the electrophoretic apparatus is mounted at a gap larger than zero from the separator and in that the electric-field system generating an electric field is formed within the gap in order to transfer sample substance from the sample feeder into the separator. In the invention therefore the transfer of the sample substance from the porous feeder portion into the separator will not be direct because the sample substance first overcomes the capillary forces by use of the electric field to enter the gap and only then penetrates the separator. The rate of migration of the electrically charged bio-molecule, in particular DNA segments, is substantially larger within the liquid filling the gap than the rate of migration in the separator, in particular separation gel. This causes a stacking effect with spatial concentration of all biomolecules at the edge of the separator in the initial stage of electrophoretic measurement. Extremely sharp bands migrating through the separation gel are present at the sequence end.

However the said gap must always be large enough to exclude direct mechanical contact between the sample feeder and the separator. To preclude crosstalk with neighboring samples, this gap however should not be unduly large. A range of 0.2 to 2 mm was found especially advantageous.

Minimal thicknesses of separator are desired to achieve highest possible sharpness of separation at little substance input. Thus gel thicknesses frequently are 0.5 mm and less. Accordingly extreme care is required to properly insert the occasionally quite flexible, porous, comb-shaped sample feeder between the plates enclosing the separator. The invention suggests in this respect that when using a separator joining two plates, at least one of the plates be beveled on the side of the separator to facilitate inserting the sample feeder. In this way trainees also may be used to insert the sample feeders.

The invention furthermore proposes filling a volume between the sample feeder and the separator with a liquid which is electrically insulating and/or of a higher density than water, preferably with a Ficoll® or a dextran solution. The accuracy of electrophoretic measurement, in particular the separation sharpness of the bands, is again improved by this step. This feature may be attributed to the increased liquid density impeding migration of the biomolecule out of the porous sample feeder, so that the biomolecules penetrate the liquid only when the electric field is applied, that is at a well defined time. The effect of using the electrically insulating liquid may be that except for biomolecule migration, ion migration does not take place, which otherwise and at least in the vicinity of the bevel might degrade electric field homogeneity and hence also resolution.

The invention also relates to a method for preparing minimal sample volumes from sample materials containing biological macromolecules, preferably such minimal volumes being then picked up by capillary action by a porous and preferably comb-shaped sample feeder.

It is easily seen that the electrophoretic sharpness of separation increases as the sample volume used decreases, namely being concentrated into an ever smaller space for instance at the ends of the comb's teeth. Only the sensitivity of detection is a lower limit on the measurement technique. However preparing such minute sample volumes for instance of 0.5 $\mu$ltr is problematical, foremost when using the desired automated pipeting system because such are able to deliver only larger sample volumes in the microliter range. The object of the invention on the other hand is to create a method leading in simple manner to minimal sample volumes, for instance in the range of 0.5 $\mu$ltr. This method is characterized by the following stages:

(a) preparing an initial sample comprising sample substance and a first volume of a first solvent liquid (preferably water), (b) preparing an interim sample by adding a second volume, of a second solvent liquid having a lower rate of evaporation than the first solvent liquid, to the initial sample, (c) evaporating the solvent liquid of the interim sample, the resultant residual volume being the desired sample volume.

Formamide was found to be an especially appropriate solvent, also because it offers further advantageous properties relative to DNA electrophoresis, namely it denatures DNA and can be used as a stop solution. Dextran is also suitable as a second solvent.

In the invention, therefore, a comparatively slight amount of second solvent is added—the sample substance being soluble in both solvent liquids. The first solvent has been evaporated after stage (c) and only the second solvent containing the sample material remains. The residual volume (which corresponds approximately to the second volume) is therefore independent of the first volume of the first liquid. The residual volume furthermore can be constrained to be less than the second volume if in stage (c) only a portion of the volume of the intermediate sample is used, for instance half. In that case the residual volume will be merely half the second volume. If for instance the initial volume of the initial sample is 4 $\mu$ltr, and 2 $\mu$ltr of stop solution consisting of 1 $\mu$ltr formamide and 1 $\mu$ltr buffer solution are added, there will be a total of 6 $\mu$ltr. If half thereof, that is 3 $\mu$ltr, are delivered into a sample pickup dish and then the whole liquid is evaporated down to the 0.5 $\mu$ltr formamide portion, there shall be a sample volume of 0.5 $\mu$ltr.

Evaporation can be accelerated using a blower such as a laboratory fan.

The resulting sample containing formamide can be picked up at once by direct contact with the porous sample feeder because being sucked into it by capillary forces. It was found that the sample feeder so prepared can be sandwiched without requiring further steps before being moved to the electrophoretic apparatus.

Before being inserted into the electrophoretic apparatus, the sample feeder is moistened in another implementation of the invention, preferably using the same liquid that also was used in the gap between the inserted sample feeder and the separator. This pre-moistening of the sample feeder precludes bubble formation in the inserted sample feeder. Such bubbles might interfere with the motion of the biomolecules.

All steps described above per se or in combination provide significantly improved sharpness of separation of individual electrophoretic bands within one electrophoretic track and also allows tracks which are narrower and more tightly adjoining, whereby a larger number of samples can be processed simultaneously in one electrophoretic measurement. Moreover handling is facilitated and it is possible to use dispensing robots.

The invention is elucidated below by preferred illustrative embodiments and in reaction to the drawings.

Figure 1:
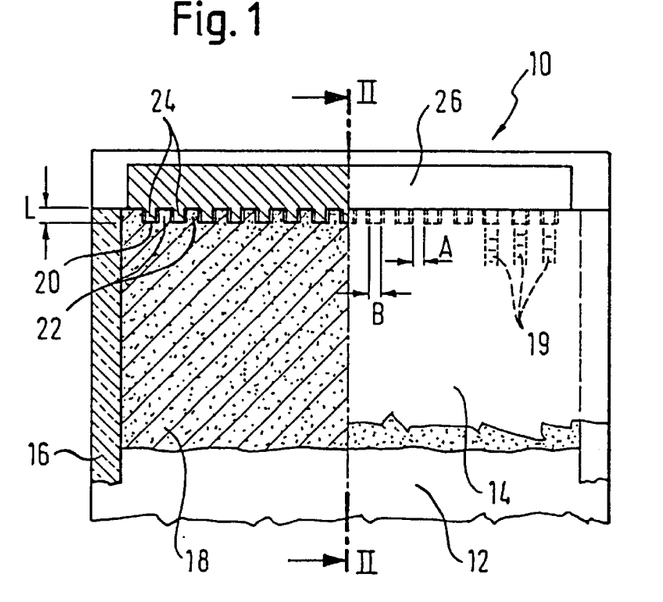
FIG. 1 is a topview and partial section along line I—I in FIG. 2 of a first embodiment of an electrophoretic apparatus with a comb-shaped sample feeder.
Figure 2:
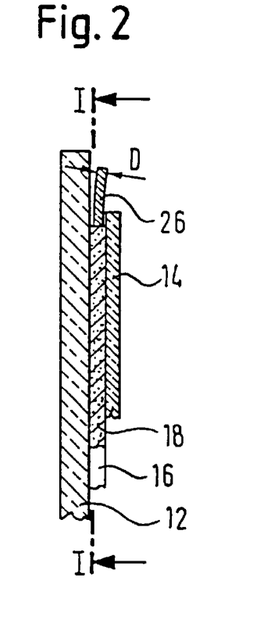
FIG. 2 is a side sectional view along line II—II of FIG. 1 of the electrophoretic apparatus of FIG. 1.

The first embodiment shown in FIGS. 1 and 2 of the sample processor of the invention, in the form of an electrophoretic apparatus, is denoted overall by 10. It comprises a first glass plate 12 and a second glass plate 14 parallel to the first one and kept apart at a defined gap by two laterally mounted spacers 16. The cavity subtended between the two glass plates 12 and 14 and spacers 16 is filled by a layer 18 of polymerized gel. Various gels may be used, for instance polyacrylic amide gels, agarose gels or hydroxy-ethyl cellulose gels. At one of its two end faces the gel layer 18 assumes a comb-like structure composed of a plurality of recesses, namely the so-called sample pickup sites 20, and of gel walls 22 located between the said recesses.

This structure is created in known manner (German patent document C2 3,024,288) by pressing a comb-like die body of a gel-repellent substance into the as yet unpolymerized gel and at appropriate locations between the two glass plates 12 and 14 of the gel layer 18 and the two spacers 16 and by keeping the gel-repellant substance there until the gel has polymerized. After having carefully removed the comb-like die there remains the desired comb-like structure of the gel end face. The expression "comb-like" herein denotes that the contour of the gel surface when seen in topview as in FIG. 1 is a linear sequence of rectangular serrations.

Projecting elements 24 of a comb-like sample feeder 26 are inserted into the sample pickup sites 20 of the gel layer 18. As shown by FIG. 2, the first glass plate 12 substantively projects beyond the second glass 14 in the end zone of the electrophoretic apparatus 10. This feature facilitates inserting the said projecting elements 24 of the sample feeder 26 into the sample pickup sites 24 provided for that purpose in the gel.

The sample feeder 26 is of thickness D less than that of the gel layer 18 (in the range of 0.1 to 0.3 mm). The length L of the elements ("teeth") 24 is about 3 to 8 mm and their width B is about 1 mm (substantially matching the depth and width of the sample pickup sites 20). The inside distance A between consecutive elements 29 in general is 1 to 3 mm corresponding to the thickness of the gel walls 22.

The sample feeder 26 is made of a porous material such as porous cellulose acetate (D=0.15 to 0.2 mm), porous polyethylene or porous glass, the pore size being such that upon contact with the sample liquid, this liquid shall be taken in by capillary force and kept inside the pores. Preferably the pore size in about 0.5 $\mu$. However depending on circumstance other materials of lesser or larger pore sizes may also be used. Because of the capillary forces, the received sample liquid then will be retained in the pores of the sample feeder 26 as long as the said liquid shall be free of forces that would overcome these capillary forces.

When applying a typical electric field to the electrophoretic apparatus 10, a force exceeding the capillary forces will be exerted on the electrically charged constituents of the sample liquid in the pores of the porous material of the sample feeder 26, whereby these constituents then depart from the sample feeder 26 to penetrate the gel layer 18 and therein migrate along the typical and mutually parallel tracks 19 which being spatially separated in relation to the particular electrical charges and mobilities in the gel. Operation of the sample feeder 26 is elucidated farther below in relation to FIG. 9.

In a variation from the above description, the sample pickup sites 20 may assume the shapes of a plurality of recesses with gel walls 22 in-between and may be prepared also in that in lieu of the comb-like shaping body made of gel-repellent material, the sample feeder 26 itself is inserted between the glass plates 12 and 14 during gel preparation. In general in this procedure a sample feeder 26 already impregnated with sample substance will be used, or a sample feeder which was dried following impregnation by the various samples. With an appropriate configuration of the sample feeder 26, for instance similar to that shown in relation to FIGS. 4 and 5 described below and comprising mutually separate material elements, it is possible furthermore to insert a sample feeder free of sample substance in the gel material, the sample substance being moved after the preparation of the gel by polymerization and before the actual measurement each time into the range of the individual material elements 24, for instance by pipeting. The transport of the sample substance into the gel zone in this instance is exclusively by capillary forces. A system operating on this principle is discussed hereunder in relation to FIG. 10.

Figure 3:
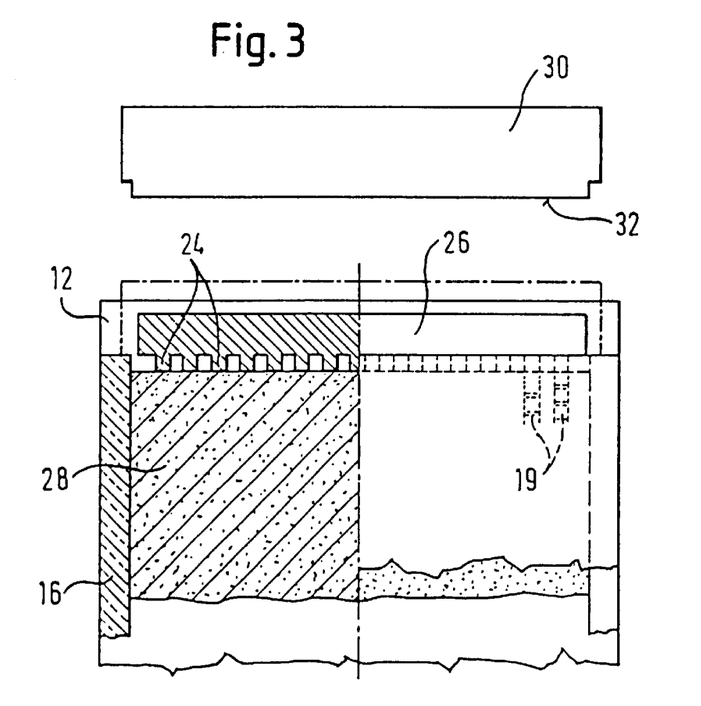
FIG. 3 is a sectional topview similar to FIG. 1 of a second embodiment with a smoothly contoured gel shaped-body.

FIG. 3 shows an electrophoretic apparatus substantially of the same design as that of FIG. 1.

However in the embodiment of FIG. 3, the end face of the gel layer 28 is fitted with a linear instead of a comb-like contour. This linear contour is prepared by forcing a suitable die 30, comprising straight or also curved end faces 32, between the two glass plates 12 and 14 into the as yet unpolymerized gel and in that this die remains there until the gel has polymerized. Following removal of the die 30 the comb-like sample feeder 26, of which the shape may correspond to that of FIGS. 1 and 2, may be moved near. In some cases the inside spacing A between consecutive elements 24 may be reduced because no account need be taken any more of adequate dimensional stability of the corresponding gel walls 22 as was the case for the embodiment of FIGS. 1 and 2. In this manner a larger number of tracks 19 may be used and a larger number of samples can be measured simultaneously. Nevertheless mixing between adjacent comb elements 24 is precluded following insertion of the sample feeder 26 because the capillary forces in the elements 24 in general prevent lateral leakage of sample liquid. It is only achieved after applying the electric field that the sample liquid exits in the direction of the field (parallel to the longitudinal direction of the tracks 19), that is, not transversely toward the adjoining comb elements 24. Furthermore the addition of electrolyte liquid into the zone of the inserted sample feeder 26 can wait until immediately before generating the electric field and as a result earlier sideways migration of sample liquid between adjacent comb elements 24 is precluded.

Figure 4:
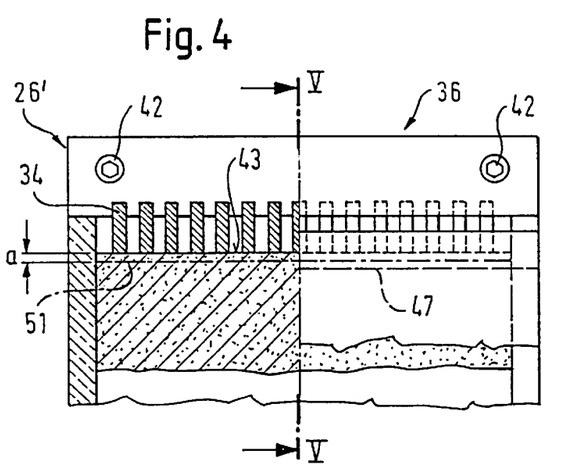
FIG. 4 is a topview with a partial section along line IV—IV of FIG. 5 of the electrophoretic apparatus but with a variant sample feeder.
Figure 5:
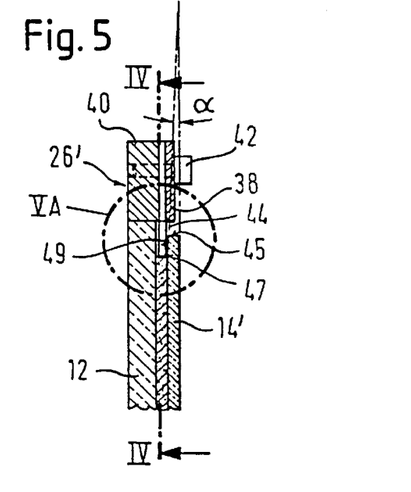
FIG. 5 is a sideview of the embodiment of FIG. 4 along the line V—V of FIG. 4.

FIGS. 4 and 5 shows a further illustrative embodiment denoted by 26'. In this instance a plurality of separate sample-feeder material elements 34 are held in place by a material element support 36. This material element support 36 is composed of two mutually parallel plates 38 and 40 which are forced against each other by two connectors 52, for instance head screws. The material elements 34 are inserted between these two plates 38 and 40. The material elements 34 are fixed in place by clamping the two plates 38 and 40 using the connectors 42.

The overall configuration of the electrophoretic apparatus of FIGS. 4 and 5 corresponds to that of FIG. 3 except for a bevel at the second glass plate 14' in the area between the gel end face 43 and the glass-plate end face 45 at the glass-plate inside facing the first glass plate 12. The bevel angle ≃ is shown in FIG. 5; the lower cross edge 47 of the bevel of FIGS. 4 and 5 is also indicated in these Figures. In this manner the sample feed zone 44 is made wedge-like to facilitate insertion of the substance elements 34 of the sample feeder 26'. This bevel of the second glass plate 14' is independent of the design of the sample feeder 26 or 26' and therefore can also be used in the apparatus of FIGS. 1 and 2 or 3.

Figure 5A:
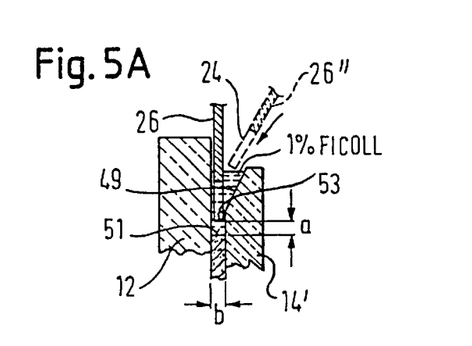
FIG. 5A is a detail VA of FIG. 5.

The detailed FIG. 5A elucidates that the bevel denoted therein by 49 facilitates insertion of the sample feeder 26 which in this case is merely shown as the laminar element of FIG. 3. An insertion position 26" is denoted by a broken contour line. Even in the presence of some corrugation of the flexible laminate fitted with the downward projecting, serrate comb elements 24, insertion is a simple operation, also at a gel thickness "b" between 0.1 and 0.3 mm. The bevel angle □ need only be selected accordingly large.

As FIG. 5A further makes plain, an especially preferred embodiment of the invention provides an inside gap "a" between the preferably linear edge 51 of the separation gel and the outer ends 53 of the projecting comb elements 24. Both the gap and the volume adjoining them upwards almost to the upper end of the plate 14 and hence reaching the bevel 49 are filled with a liquid containing 1% Ficoll® and correspondingly denoted in FIG. 5A. This liquid on one hand is electrically insulating (ie a dielectric liquid) and on the other hand its density exceeds that of water. The expression Ficoll® means copolymers made of saccharose and epichlorohydrine and of a molecular weight between 70,000 and 400,000.

Because of the initially discussed stacking effect, the electrophoretic bands are especially sharp. The Ficoll® solution ensures a homogeneous electric field in spite of the wedge-shape of the space above the separation gel caused by the bevel 49. To show clearly the gap "a" of FIG. 5A, it is also shown as a possible variant in FIG. 4; therein the upper separation-gel edge shown in dashed lines also is denoted by 51. It is clear that the edge 51 is linear (contrary to the embodiment of FIGS. 1 and 21 and thus simplifies preparation and allows a larger number of samples (that is serrate elements 24).

The use made as shown in FIG. 5 of a plurality of separate porous material elements affixed in a material-element support 36 offers the advantage that the gap between and the number of material elements 34 can be individually matched to different sample conditions. Moreover sample substance migration through the porous material from material element to material element is inherently precluded.

Other structures of the sample feeder 26, 26' are conceivable, for instance using a material element support in the form of a substrate sheet illustratively in comb-shape and again bearing a corresponding number of individual material elements 34 or a sheet also of comb-shape and made of a porous material.

Figure 6:
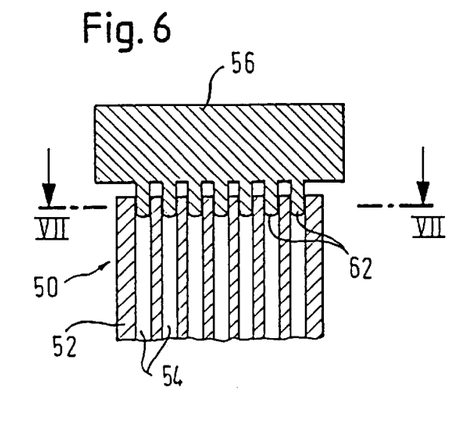
FIG. 6 is a sectional topview along line VI—VI of a third embodiment of the electrophoretic apparatus comprising several separation capillaries and with a corresponding sample feeder.
Figure 7:
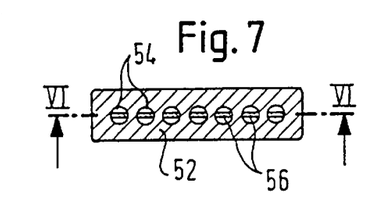
FIG. 7 is a sectional view along line VII—VII of the apparatus of FIG. 6.

FIGS. 6 and 7 show another embodiment of the invention wherein the electrophoretic apparatus 50 is not fitted with a planar, continuous gel, but instead with a plurality of gel-filled separation capillaries 54 inside a base body 52. The projecting elements 62 of a comb-like sample feeder 56 are inserted into the apertures of the separation capillaries 54, the said sample feeder 56 being either as shown, that is as a single sheet of porous material, or, as shown in FIGS. 4 and 5, being composed of a material element support with a plurality of separate, porous material elements. The porous, comb-like sample feeder 56 also in this case facilitates sample delivery to a plurality of tightly arrayed sample pickup sites (here the apertures of the separation capillaries 54) even through in this case as well the danger of mixing sample liquid from neighboring sample pickup sites ("crosstalk") is anyway slight. The insertion of the free ends of the elements 62 into the apertures of the separation capillaries 54 can be facilitated by flaring or rounding the elements 62, or, (in omitted manner similarly to the case of FIG. 5), by correspondingly conically flaring the separation-capillary apertures. Advantageously, in this as well as in the other embodiments, all elements 62 deliver practically simultaneously their sample liquid to the particular sample pickup sites and as a result there is no danger that several samples' liquids prematurely might be delivered to the particular sample pickup sites, as might happen in sequential sample delivery for instance by pipeting. Moreover and in most cases, the capillary forces assure that sample liquid shall issue only from the porous material if a sufficiently intense electric field has been applied. Lastly the beginning of diffusion can be delayed by accordingly delaying the addition of electrolyte.

Figure 8:
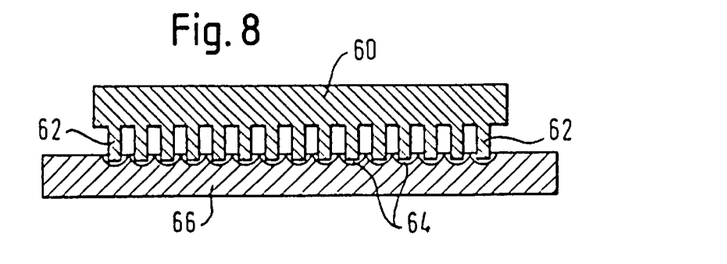
FIG. 8 is a sectional front view of a comb-shaped sample feeder inserted into the sample wells of a sample vessel rack.

The comb-like sampler feeder described above in its various embodiments of one sheet of porous material or porous material elements also allows simple and quick pickup of sample liquid by the sample feeder. This purpose is served by sample vessel rack 66, sectionally shown in simplified manner in FIG. 8 and comprising a plurality of sample wells 64. These wells geometrically match the projecting elements (teeth) 62 of the sample feeder 60. If, as shown, the teeth are arrayed linearly and sequentially, then the sample wells 64 are also commensurately arrayed in linear sequence. Accordingly all elements 62 of the sample feeder can be simultaneously impregnated with sample liquid by correspondingly dipping in the sample wells 64. Following impregnation of the elements 62, the sample feeder 60 is then moved toward the particular electrophoretic apparatus. Filling the sample vessel rack 66 can take place beforehand for instance using a corresponding manual or automated multi-pipet system, that is independently of the actual sample delivery to the electophoretic apparatus using the sample feeder 60.

As discussed above, using the sample feeder fitted with the porous elements to pick up and retain sample liquid, this sample liquid can be moved in simple manner to the particular electrophoretic apparatus, then allowing the mutual spacing between the adjacent, porous elements and hence also the spacing between individual samples to be kept small, as a result of which the measurement effectiveness of the electrophoretic apparatus is substantially increased. Simultaneous beginning of migration of the electrically charged constituents of the sample liquid is assured at the beginning of electrophoresis and consequently there will be high accuracy of electrophoretic measurement, especially when comparing adjoining tracks.

Independently of the above, using porous material to pick up sample liquid also allows processing the sample liquid within the porous material. Accordingly the porous material simultaneously acts as a sample receptacle or as a reaction vessel. For that purpose the porous material may be impregnated consecutively or at its different sites with the liquids to be reacted, in the latter case mixing taking place in the porous material on account of capillary forces. Moreover the porous material may be impregnated beforehand with at least one of the reaction liquids and then be dried, the porous material then being correspondingly "impregnated". Thereupon the porous material can be dipped at an arbitrary later time into the other reagent liquid, for instance the sample liquid and/or further solutions of reagents in order to implement the desired reaction.

The reaction may be an arbitrary biochemical reaction, for instance an enzyme reaction, a nucleic-acid/hybridization reaction, an immuno-chemical reaction or the like. Preferably nucleic-acid reactions are carried out, for instance an in-vitro transcription, whereby an RNA strand is produced by an RNA polymerase at a nucleic-acid matrix, a sequencing whereby, preferably by enzyme reactions for instance with T7 DNA polymerase, the nucleotide sequence of a nucleic acid will be determined, or amplification, whereby the quantity of nucleic acid present in the sample liquid can be increased. A preferred example of amplification is PCR (polymerase chain reaction). It comprises three consecutive reaction stages, namely a reaction splitting the DNA into individual strands, a hybridization reaction and an enzyme nucleic-acid elongation. Typically several cycles of these reaction stages are carried out for one PCR, preferably 20 to 30 cycles, achieving thereby high multiplication of the desired nucleic acid. Preferably PCR is carried out at raised temperature, the enzyme reaction being run at 65 to 80° C., especially preferred at 72 to 75° C., and the splitting reaction at 80 to 100° C., especially preferred at 90 to 95° C. Such procedures also are called thermocycling with thermally stable enzymes. Sensitivity of sample analysis can be considerably increased by PCR or another amplification reaction.

Surprisingly the porous material withstands the drastic thermocycling conditions without ensuing analysis or isolation of the reaction product being significantly degraded by decomposition of the porous material.

The combination of the just above described procedure with the methods initially described is particularly advantageous, that is, following the said reactions in the porous material, this material can then be moved toward a sample processor for evaluation of the reaction results. An electrophoretic apparatus is used in the above described embodiments. However other analyzers might also be used, for instance chromatographic devices or a mass spectrograph.

This procedure will be discussed below in relation to FIG. 9.

Figure 9:
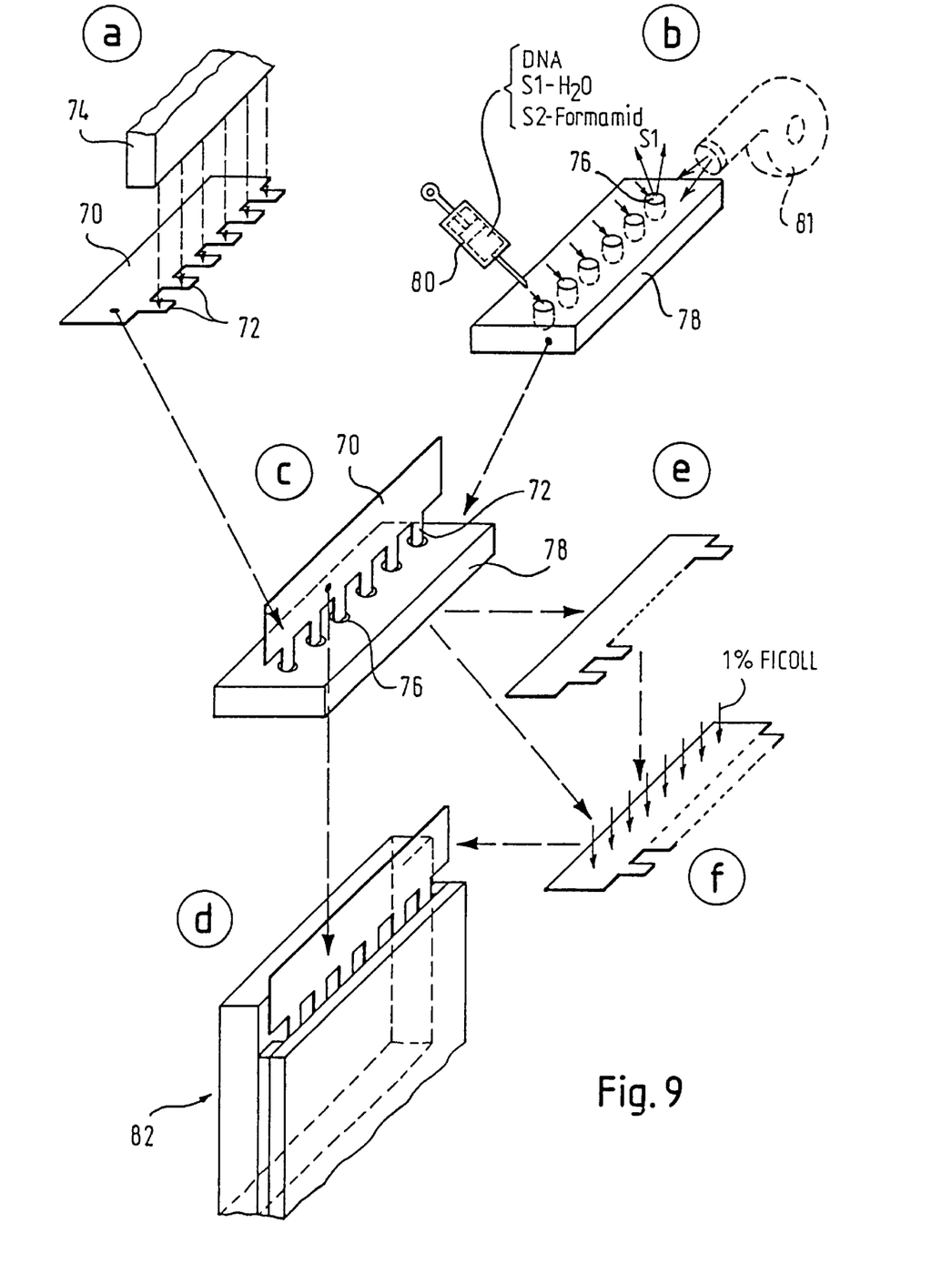
FIG. 9 illustrates the method stages characterizing the operation of the sample feeder.

FIG. 9a shows a comb-like sample feeder 70 in the form of a porous sheet. The projecting elements 72 of the sample feeder are impregnated by a meter 74 with appropriate reagents such as dyes, enzymes, nucleic acids or the like. These reagents facilitate analysis of the sample liquid by staining, increasing resolution or similar, or they are added to initiate specific chemical or biochemical reactions before analysis or to retain certain sample portions. This procedure also can be carried out several times consecutively using different reagents in order to thereby prepare the porous material elements 72 of the sample feeder 60 for a given sample analysis. Where called for the sample feeder is temporarily stored until the reagents in the porous material have dried.

FIG. 9b shows how the recesses 76 of a sample vessel rack 78 are each filled separately with sample liquid using one pipet 80. This procedure also may be automated using a corresponding plural pipeting system.

As shown in FIG. 9c, after the well 76 of the sample vessel rack 78 has been filled, the porous sample feeder 70 is inserted by its projecting elements 72 into the corresponding wells 76 of the sample vessel rack 78. In the process the pores of the porous material of the sample feeder 70 aspirate sample liquid to completion (sample delivery). When thereupon the projecting elements 72 of the sample feeder 70 are removed from the wells 76, the sample liquid remains in the pores of the particular elements 72 on account of capillarity. In this manner sample liquid can be moved from the sample vessel rack 78 to the sample processor 82 for instance in the form of an electrophoretic or chromatographic apparatus as shown in FIG. 9d.

FIG. 9b schematically shows a special kind of preparation of particularly small sample volumes, illustratively in the range of 0.5 μltr. An initial sample is prepared in an omitted first stage (a) and comprises the biological substance to be tested, in particular DNA fragments, further a first volume of a solvent liquid S1, preferably water. The volume may be 4 μltr for instance. Thereupon 0.2 μltr of a stop solution are added in a stage (b), said stop solution consisting again of 1 μltr of a second solvent liquid (formamide [formic acid amide]) and 1 μltr of a buffer solution. The resultant interim sample of 6 μltr is picked up by the automated pipet system and half of it (3 μltr) is filled into the particular, dish-shaped well 76 of the sample well rack 78. Next the first solvent liquid (water) is evaporated preferably with the support of a blower 81 indicated in dashed lines in FIG. 9b. FIG. 9b further indicates by the corresponding arrows the removal of the first solvent liquid S1. The second solvent liquid S2 (formamide) remains behind and also contains the DNA fragments. The sample volume corresponding to the formamide portion amounts merely to 0.5 μltr.

As already discussed, these sample volumes may be picked up by immersing the teeth of the sample feeder 70, the pre-treatment of this sample feeder 70 of FIG. 9a also being eliminated where appropriate.

Using the second solvent liquid S2 of comparatively lower rate of diffusion makes it possible to also to temporarily store (FIG. 9e) the correspondingly impregnated sample feeder 70 before it is moved to the electrophoretic or chromatographic apparatus of FIG. 9d.

Regardless of the sample feeder 70 being temporarily stored or not, it will be advantageously moistened, as indicated in FIG. 9f, directly before being inserted into the electrophoretic or chromatographic apparatus. Such moistening prevents air bubbles, which might degrade measurement, from forming after the sample feeder 70 has been inserted into the electrophoretic or chromatographic apparatus. The same liquid may be used for moistening that also was used in the gap zone of FIG. 5A. Preferably this liquid shall be a 1% Ficoll® solution. The consequence of pre-moistening the sample feeder 70 with the 1–10% Ficoll® solution or dextran solution is that the buffer solution wetting the sample feeder 70 at its side away from the separation gel shall flow only later through the porous sample feeder, which might degrade measurement.

The sample processor 82 may assume various designs. All previously described embodiments are applicable. By adjusting the pH value and by means of an effective pH buffer, the sample liquid is prepared in such a way that the biomolecules contained in it, for instance proteins, will be electrically charged. The capillary forces keeping the sample liquid in the sample feeder 70 are overcome by applying an adequately high electric voltage which thereby also induces motion of the charged molecules in relation to the electric forces acting on them. When the electric field is applied, the sample liquid may either enter the gel layer by direct contact between the sample feeder 70 and the gel layer of the sample processor 82, or it may enter said gel layer by means of a suitable electrolyte solution, and in the latter case there may be a distance up to a few mm between the sample feeder and the gel layer.

Because of the sensitivity of conventional electrophoretic apparatus, already slight amounts of sample liquid suffice to impregnate the projecting elements 72 of the sample feeder 70. Obviously excessive amounts of sample liquid must be avoided to prevent sample liquid from moving by means of the porous material itself from one element 72 to the next one.

As a practical manner it was found that "crosstalk" between the elements 72 by capillarity through the porous material is precluded per se at those comparatively small sample quantities. Moreover the electric field used in electrophoresis practically ensures that the full quantity of sample liquid shall exit the particular element 72. Therefore it is advantageously feasible also to severally use one sample feeder 70. In this process, several rows of sample may be also fed in time sequence into the same gel if the sample feeder 70 is moved at a corresponding time delay, in each case loaded with new sample liquids, to the electrophoretic apparatus. Because of the interim migrations of the rows of samples, the latter are mutually offset spatially, that is, they are mutually spaced apart in the direction of the electric field.

Moreover the porous material is appropriate to transmit sample liquid to otherwise only poorly accessible sample pickup sites. Such a case illustratively is delivery of sample liquid to a microchip system, in particular to a DNA sensor, as indicated in much simplified manner in FIG. 10.

Figure 10:
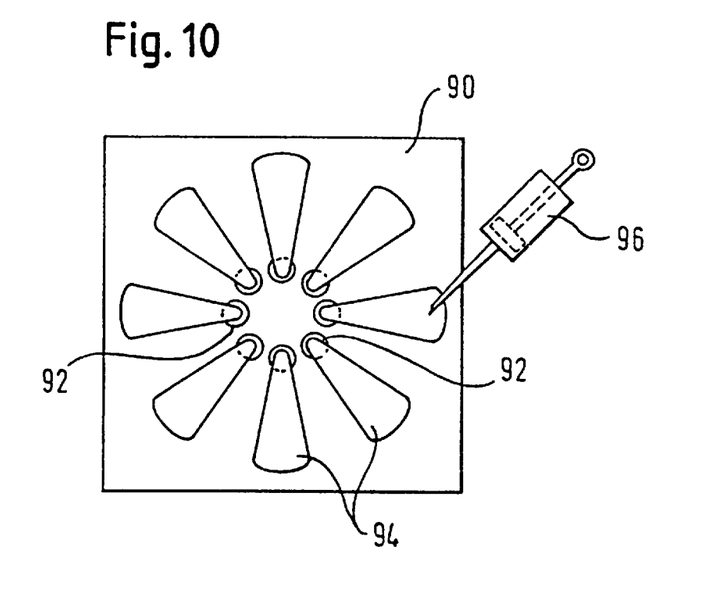
FIG. 10 shows the operation of separate sample feeder segments to move sample liquid to a circularly configured microchip system fitted with DNA sensors.

Various sensor zones 92 are present on a support 90 and being small (for instance 2×2 mm), are hardly accessible to sample liquid. However, when using separate, porous sample feeders 94, sample delivery is very easily implemented. By adding sample liquid with a pipet 96 to comparatively large-surface zones of the porous sample feeders 94, with ensuing migration of the sample liquid in this porous material caused by capillarity toward the microzones, controlled sample liquid delivery can be achieved.

In lieu of radial configurations of the separate sample feeders 94, another arbitrary geometry also may be selected, for instance with mutually parallel feeder lengths varying from feeder to feeder. In this manner the distance between the delivery ends of the sample feeders can be enlarged. In this configurations ,too, the transmission of the sample material from the sample feeder to the particular sensor zone can be constrained by an appropriate electric field.

Figure 11:
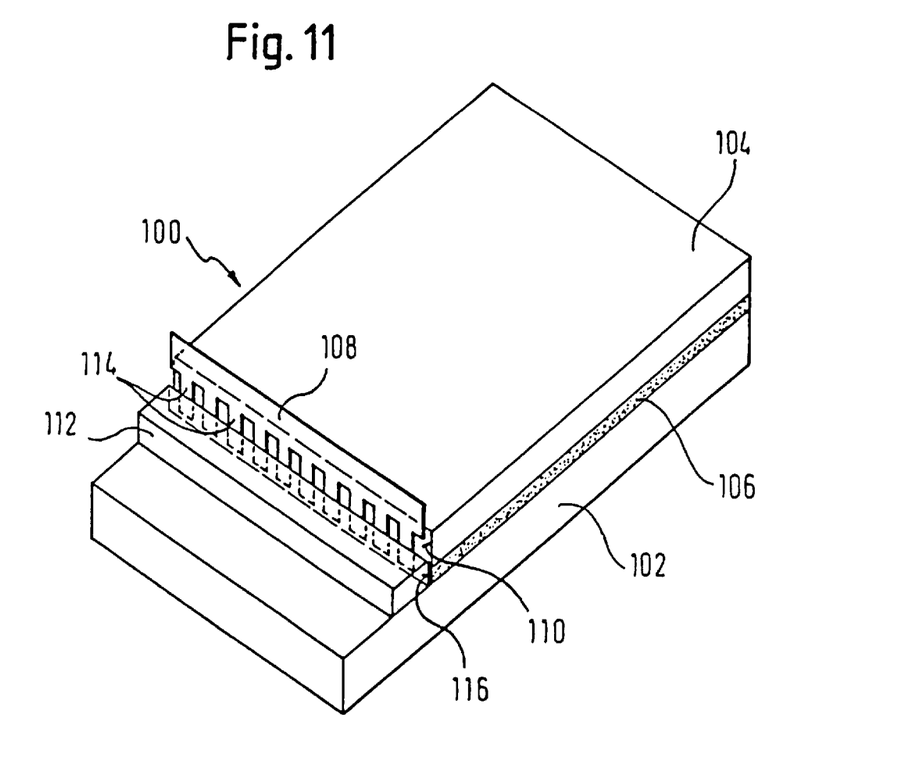
FIG. 11 is a simplified isometric view of a further variant of an electrophoretic apparatus with sample feeder.

FIG. 11 shows a simplified further electrophoretic apparatus composed of a lower glass plate 102, an upper glass plate 104 and a sandwiched gel layer 106 which in this case extend as far as the left lower end of the upper glass plate 104 of FIG. 11. This configuration simplifies gel preparation. Also it makes it possible to mount the again comb-like sample feeders 108 essentially perpendicularly to the (here horizontal) plane of the gel layer 106. Again as was the case for the previously described electrophoretic apparatus, the electrophoretic apparatus 100 shown in FIG. 11 also can be operated at an arbitrary spatial orientation because, unlike the case for conventional electrophoretic apparatus with sample receiving wells at the gel edge, there is no danger in the case of the invention that the sample substance should leak out. As already indicated several times, the porous material retains within it the sample substance by capillarity; directed migration of the sample substance into the gel is assured only upon application of the electric field.

In order to keep the comb-like sample feeder 108 in the shown position in abutment against the end faces 110 of the upper (comparatively shorter) glass plate 104, a support bracket 112 may be used as shown to form a gap substantially corresponding to the thickness of the sample feeder 108 between itself and the end face 110. In this manner the ends of the material elements ("teeth") 114 of the sample feeder 108 that are loaded with sample substance are kept either directly at the corresponding end face 116 of the gel layer 106 or at a slight distance away. After delivering electrolyte and turning ON the electric field, the desired directed migration of the sample substance from the sample feeder 108 into the gel layer 106 takes place (sample delivery). Because the teeth of the sample feeder 108 no longer need being threaded between the tightly neighboring glass plates 104 and 106, handling is simplified again.

Be it also borne in mind as regards the general design of the above described various electrophoretic apparatus that the electric field is set up by a cathode and an anode respectively in the vicinity of the end zones of the gel layer and at the edge of the sample feeder away from the gel.

What is claimed is:

1. A method for moving a sample by a sample feeder to a sample processor comprising the steps of:
   (a) providing a sample comprising a biological macromolecule;
   (b) providing the sample feeder comprising a sample pickup site and contacting the sample with the sample feeder for uptake of the sample through the sample pickup site;
   (c) moving the sample to a sample delivery site on a sample processor; and
   (d) delivering the sample from the sample feeder through the sample delivery site for processing of the sample by the sample processor, wherein the sample feeder comprises at least one porous material element comprising a porous material of a pore size wherein upon contacting the sample the sample is retained by capillary forces in a liquid phase in the porous material and wherein a gap different from zero exists between the at least one porous material element of the sample feeder and the sample delivery site.

2. Method as claimed in claim 1, wherein following sample pickup by the sample feeder the sample is dried, and the sample feeder is moved toward a liquid phase before sample delivery.

3. Method as claimed in claim 1, wherein an electric field crossing the porous material element is generated in the region of the sample pickup site in order to produce a flow from the porous material element.

4. Method as claimed in claim 1, wherein following delivery of the sample, the sample feeder is moved from the sample delivery site to the sample pickup site.

5. Method as claimed in claim 1, wherein the porous material element of the sample feeder physically connects the sample delivery site to the sample pickup site.

6. Method as claimed in claim 1, comprising a sample processor comprising a plurality of sample pickup sites and a corresponding plurality of porous material elements of the sample feeder.

7. Method as claimed in claim 6 , wherein the sample feeder comprises a material element support supporting the material elements in a configuration corresponding to the geometry of the sample pickup sites.

8. Method as claimed in claim 7, wherein the sample feeder is comb-shaped.

9. Method as claimed in claim 7, wherein the sample feeder is a porous sheet comprising porous material elements.

10. Method as claimed in claim 7, wherein the material element support bears a corresponding plurality of separate material elements.

11. Method as claimed in claim 7, wherein the material element support consists of a substrate sheet.

12. Method as claimed in claim 6, comprising a sample vessel rack with a plurality of sample wells in a configuration corresponding to the geometric array of the material elements of the sample feeder.

13. Method as claimed in claim 12 comprising sample slots formed along an edge of a separator at the sample pickup sites in the separator, wherein the separator simultaneously separates several sample liquids, and the sample slots comprise receiving matching porous material elements of the sample feeder.

14. Method as claimed in claim 13, wherein the sample slots are prepared independently of the sample feeder and before moving the sample feeder, or are prepared by inserting the sample feeder already fitted with sample substance into the separation gel material before polymerization.

15. Method as claimed in claim 12, wherein the sample feeder is mounted in the direction of the separator edge at a distance of up to a few mm from the edge.

16. Method as claimed in claim 15, wherein the material elements are mounted in a common and substantially planar surface located either in the plane of the separator or being perpendicular to the separator.

17. Method as claimed in claim 2, comprising a porous material with a mean pore size less than 100μ.

18. Method as claimed in claim 17, comprising a porous material with a mean pore size between 1.5 and 0.2μ.

19. Method as claimed in claim 1 comprising a porous material comprising at least one of porous cellulose acetate, cellulose mixed ester, porous polyethylene of porous glass, agarose gel and other wide-mesh gel matrices.

20. Method as claimed in claim 1, wherein the pH value of the liquid phase electrically charges biological macromolecules in the sample liquid.

21. Method as claimed in claim 1, wherein the sample feeder is moved several times consecutively to move sample liquid.

22. Method as claimed in claim 1, comprising moving sample liquid to an electrophoretic apparatus or to a chromatographic apparatus.

23. Method as claimed in claim 22, wherein the electrophoretic apparatus comprises a horizontally or vertically oriented separator.

24. Method as claimed in claim 1, comprising moving the sample liquid to an electrophoretic apparatus or a chromatographic apparatus comprising several separation capillaries.

25. Method as claimed in claim 1, comprising moving the sample liquid to a microchip system comprising several sensors.

26. Method as claimed in claim 1, wherein the gap distance is up to several mm.

27. Sample feeder according to the method claimed in claim 1, comprising at least one porous material element.

28. Electrophoretic apparatus fitted with a sample feeder for performing the method claimed in claim 1.

29. Method as claimed in claim 1, wherein the gap distance is between 0.2 and 2 mm.

30. Electrophoretic apparatus fitted with a porous sample feeder, comprising a separator and an electric field system to apply an electric field to the separator wherein the porous sample feeder is inserted into the electrophoretic apparatus at a gap different from zero from the separator, and the electric field system is adapted to generate an electric field around the gap to move sample material from the sample feeder into the separator.

31. Electrophoretic apparatus as claimed in claim 30, wherein the gap is 0.2 to 2 mm.

32. Electrophoretic apparatus as claimed in claim 30, comprising a separator joining two plates to each other, wherein at least one of the plates is fitted with a bevel on the side of the separator for inserting the sample feeder.

33. Electrophoretic apparatus as claimed in claim 30, wherein a volume between the sample feeder and the separator is filled with a liquid which is electrically insulating and/or of a higher density than water.

34. Electrophoretic apparatus as claimed in claim 33, wherein the volume adjoins the bevel.

35. A method for preparing and picking up small sample volumes of a sample material containing biological macromolecules comprising the steps of:

(a) providing a sample comprising the sample material such as DNA comprising the biological macromolecules and a volume of a first solvent liquid, (b) adding a volume of a second solvent liquid of a lesser rate of evaporation than the first solvent liquid to the sample, (c) evaporating the first solvent liquid from the sample of b) to obtain the small sample volume, and (d) picking up the sample by a porous sample feeder.

36. Method as claimed in claim 35, comprising a blower in stage (c).

37. Method as claimed in claim 35, wherein a portion of the second sample is used in stage (c).

38. Method as claimed in claim 35, wherein the second solvent liquid is formamide.

39. Method as claimed in claim 35, wherein following pickup of the sample volume by the porous sample feeder and before insertion of the sample feeder into an electrophoretic apparatus, the sample feeder is moistened.

40. Method as claimed in claim 39, wherein the porous sample feeder is stored.

41. Method as claimed in claim 35, wherein the sample volume is approximately 0.5 μl.

* * * * *